(12) United States Patent
Gambhir et al.

(10) Patent No.: US 8,574,547 B2
(45) Date of Patent: Nov. 5, 2013

(54) PHOTOACOUSTIC PROBES AND METHODS OF IMAGING

(75) Inventors: Sanjiv S. Gambhir, Portola Valley, CA (US); Levi Jelena, Palo Alto, CA (US); Shay Keren, Haifa (IL)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 663 days.

(21) Appl. No.: 12/595,525

(22) PCT Filed: Apr. 10, 2008

(86) PCT No.: PCT/US2008/059925
§ 371 (c)(1),
(2), (4) Date: Oct. 12, 2009

(87) PCT Pub. No.: WO2008/124834
PCT Pub. Date: Oct. 16, 2008

(65) Prior Publication Data
US 2010/0111871 A1  May 6, 2010

Related U.S. Application Data

(60) Provisional application No. 60/922,603, filed on Apr. 10, 2007.

(51) Int. Cl.
*A61K 49/00* (2006.01)
*A61B 5/00* (2006.01)
*A61B 8/00* (2006.01)
*A61B 10/00* (2006.01)

(52) U.S. Cl.
USPC .............................................. 424/9.1; 424/9.6

(58) Field of Classification Search
USPC ........................................................ 424/9.1
See application file for complete search history.

(56) References Cited

U.S. PATENT DOCUMENTS 5,622,821 A * 4/1997 Selvin et al. ................. 435/6.11
6,592,847 B1 * 7/2003 Weissleder et al. ............ 424/9.6

* cited by examiner

*Primary Examiner* — Michael G Hartley
*Assistant Examiner* — Melissa Perreira
(74) *Attorney, Agent, or Firm* — Thomas Horstemeyer, LLP

(57) ABSTRACT

Embodiments of the present disclosure provide for photoacoustic probes, methods of determining the presence and location of a specific target, methods of determining the presence and location of an enzyme, methods of determining the presence and location of a specific target and an enzyme, and the like.

6 Claims, 7 Drawing Sheets

SEQ ID NO: 1

Arg-Arg-Arg-Arg-Arg-Lys-Pro-Leu-Gly-Val-Arg-Cys-NH2

Cell penetrating peptide     MMP-2 cleavable sequence

WHICH QUENCHER SHOULD I USE?

| DYE NAME | EX | Em | COLOR | BHQ BASED ON J(λ) | OTHER DARK QUENCHERS: | | |
|---|---|---|---|---|---|---|---|
| ALEXA 350 | 346 | 442 | BLUE | | | | |
| PACIFIC BLUE | 416 | 451 | BLUE | | | | |
| MARINA BLUE | 362 | 459 | BLUE-GREEN | BHQ-0 λ(max)=495 nm RANGE = 430-520 nm | DABCYL λ(max) = 479 nm | | QSY-35 λ(max) = 475 nm |
| ACRIDINE | 362 | 462 | BLUE-GREEN | | | | |
| EDANS | 336 | 468 | GREEN | | | ECLIPSE λ(max) = 522 nm | |
| COUMARIN | 432 | 472 | GREEN | | | | |
| BODIPY 493/503 | 493 | 503 | GREEN | | | | |
| CY2 | 489 | 506 | GREEN | | | | |
| BODIPY FL-X | 504 | 510 | YELLOW-GREEN | | | | |
| DANSYL | 335 | 518 | YELLOW-GREEN | | | | |
| ALEXA 488 | 495 | 519 | YELLOW-GREEN | | | | |
| FAM | 495 | 520 | YELLOW-GREEN | | | | |
| OREGON GREEN | 500 | 520 | YELLOW-GREEN | | | | |
| RHODAMINE GREEN-X | 503 | 528 | YELLOW-GREEN | | | | |
| NBD-X | 466 | 535 | YELLOW-GREEN | BHQ-1 λ(max)=534 nm RANGE = 480-580 nm | | | |
| TET | 521 | 536 | YELLOW-GREEN | | | | |
| ALEXA 430 | 434 | 541 | YELLOW-GREEN | | | | |
| BODIPY R6G-X | 529 | 547 | YELLOW | | | | |
| JOE | 520 | 548 | YELLOW | | | | |
| YAKIMA YELLOW | 531 | 549 | YELLOW | | | | |
| ALEXA 532 | 532 | 554 | YELLOW | | | | |
| VIC | 538 | 554 | YELLOW | | | | |
| HEX | 535 | 556 | YELLOW | | QSY-7&9 λ(max) = 560 nm | | |
| R6G | 524 | 557 | YELLOW | | | | |
| ALEXA 555 | 555 | 565 | YELLOW-ORANGE | | | | |
| BODIPY 564/570 | 563 | 569 | YELLOW-ORANGE | | | | |
| BODIPY TMR-X | 544 | 570 | YELLOW-ORANGE | | | | |
| CY3 | 550 | 570 | YELLOW-ORANGE | | | | |
| ALEXA 546 | 556 | 573 | YELLOW-ORANGE | | | | |
| TAMRA | 555 | 576 | YELLOW-ORANGE | | | | |
| RHODAMINE RED-X | 560 | 580 | YELLOW-ORANGE | BHQ-2 λ(max)=579 nm RANGE = 550-650 nm | | | |
| BODIPY 581/591 | 581 | 591 | YELLOW-ORANGE | | | | |
| REDMOND RED | 579 | 595 | YELLOW-ORANGE | | | | |
| CY3.5 | 581 | 596 | YELLOW-ORANGE | | | | |
| ROX | 575 | 602 | ORANGE | | | | |
| ALEXA 568 | 578 | 603 | ORANGE | | | | |
| CAL RED | 583 | 603 | ORANGE | | | | |
| BODIPY TR-X | 588 | 616 | ORANGE-RED | | | | |
| ALEXA 594 | 590 | 617 | ORANGE-RED | | | | |
| BODIPY 630/650-X | 625 | 640 | RED | | | | |
| LC RED 640 | 625 | 640 | RED | | | | |
| ALEXA 633 | 632 | 647 | RED | | QSY-21 λ(max) = 661 nm | | |
| BODIPY 650/665-X | 646 | 660 | RED | | | | |
| ALEXA 647 | 650 | 665 | RED | | | | |
| CY5 | 649 | 670 | RED | BHQ-3 λ(max)=680 nm RANGE = 620-730 nm | | | |
| ALEXA 660 | 663 | 690 | FAR RED | | | | |
| CY5.5 | 675 | 694 | FAR RED | | | | |
| ALEXA 680 | 679 | 702 | FAR RED | | | | |
| LC RED 705 | 689 | 705 | FAR RED | | | | |
| ALEXA 700 | 702 | 723 | FAR RED | | | | |
| ALEXA 750 | 749 | 775 | FAR RED | | | | |

FIG. 10

PHOTOACOUSTIC PROBES AND METHODS OF IMAGING

CROSS-REFERENCE TO RELATED APPLICATION

This application claims priority to "Photoacoustic Probes and Methods of Imaging," having serial number PCT/US2008/059925, filed on Apr. 10, 2008. This application claims priority to the following U.S. provisional application: "Photoacoustic Probes and Methods of Imaging," having Ser. No. 60/922,603, filed on Apr. 10, 2007; which is entirely incorporated herein by reference.

STATEMENT REGARDING FEDERALLY SPONSORED RESEARCH OR DEVELOPMENT

This invention was made with Government support under contract CA119367 awarded by the National Institutes of Health. The Government has certain rights in the invention.

BACKGROUND

Photoacoustic techniques are investigative methods in which excitation laser pulses are absorbed in a target absorber producing an acoustic response. These acoustic waves act as carriers of information relating to the light absorption properties of the target absorber and can be used to describe its constituents and structure. Applications include the characterization of biological tissue and non-destructive testing of materials and structures. While photoacoustic techniques provide an inherently powerful means of characterizing a target, their practical implementation can be problematic using conventional acoustic methods.

SUMMARY

Embodiments of the present disclosure provide for photoacoustic probes, methods of determining the presence and location of a specific target, methods of determining the presence and location of an enzyme, methods of determining the presence and location of a specific target and an enzyme, and the like.

One exemplary photoacoustic probe, among others, includes: a targeting moiety and a non-fluorescent absorber compound, wherein the targeting moiety is linked to the non-fluorescent absorber compound, and wherein the non-fluorescent absorber compound has the characteristic of being able to absorb optical energy and being able to convert the absorbed energy to thermal energy to produce an acoustic signal.

Another exemplary photoacoustic probe, among others, includes: a targeting moiety, a fluorescent compound, and a non-fluorescent absorber compound, wherein the targeting moiety is linked to the fluorescent compound and the non-fluorescent absorber compound.

Another exemplary photoacoustic probe, among others, includes: a targeting moiety, a non-fluorescent absorber compound, an enzyme cleavable linker, and a fluorescent compound, wherein the targeting moiety is linked to the non-fluorescent absorber compound and the enzyme cleavable linker, while the enzyme cleavable linker is linked to the fluorescent compound.

One exemplary method of determining the presence and location of a specific target, among others, includes: introducing a photoacoustic probe to a system, wherein the system is selected from a sample or a host, wherein the photoacoustic probe includes a specific targeting moiety and a non-fluorescent absorber compound, wherein the photoacoustic probe interacts with the specific target because the specific targeting moiety has an affinity for the specific target, wherein the non-fluorescent absorber compound has the characteristic of being able to absorb optical energy and being able to convert the absorbed energy to thermal energy to produce an acoustic signal; illuminating the system with an optical energy; and generating an acoustic signal.

One exemplary method of determining the presence and location of an enzyme, among others, includes: introducing a photoacoustic probe to a system, wherein the system is selected from a sample or a host, wherein the photoacoustic probe includes a non-specific targeting moiety, a non-fluorescent absorber compound, an enzyme cleavable linker, and a fluorescent compound, wherein the non-specific targeting moiety is linked to the non-fluorescent absorber compound and the enzyme cleavable linker, while the enzyme cleavable linker is linked to the fluorescent compound; and illuminating the system with an optical energy, wherein if the system includes an enzyme that interacts with the enzyme cleavable linker causing the fluorescent compound to be released from the photoacoustic probe, then an acoustic signal is produced because the optical energy is absorbed by the non-fluorescent absorber compound and is converted to thermal energy to produce the acoustic signal, and wherein if the system does not include the enzyme, then a fluorescent signal is produced by the fluorescent compound.

One exemplary method of determining the presence and location of a specific target and an enzyme, among others, includes: introducing a photoacoustic probe to: a sample or host, where the photoacoustic probe includes a specific targeting moiety, a non-fluorescent absorber compound, an enzyme cleavable linker, and a fluorescent compound, wherein the specific targeting moiety is linked to the non-fluorescent absorber compound and the enzyme cleavable linker, while the enzyme cleavable linker is linked to the fluorescent compound; and illuminating the system with an optical energy, wherein if the system includes an enzyme that interacts with the enzyme cleavable linker causing the fluorescent compound to be released from the photoacoustic probe, then an acoustic signal is produced because the optical energy is absorbed by the non-fluorescent absorber compound and is converted to thermal energy to produce an acoustic signal, wherein if the system does not include the enzyme, then a fluorescent signal is produced by the fluorescent compound.

These embodiments, uses of these embodiments, and other uses, features and advantages of the present disclosure, will become more apparent to those of ordinary skill in the relevant art when the following detailed description of the preferred embodiments is read in conjunction with the appended figures.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 10 is a table that shows fluorescent compound and the non-fluorescent absorber compound.

DETAILED DESCRIPTION

Figure 1:
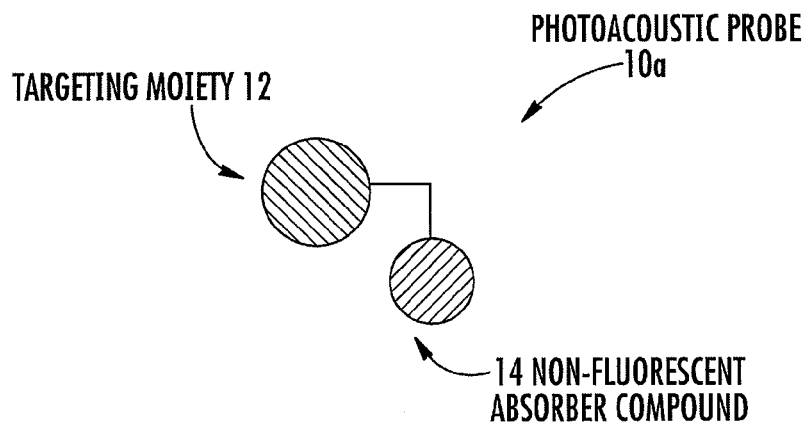
FIG. 1 illustrates an embodiment of the photoacoustic probe.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of synthetic organic chemistry, biochemistry, biology, molecular biology, recombinant DNA techniques, pharmacology, imaging, and the like, which are within the skill of the art. Such techniques are explained fully in the literature. In particular, See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984), each of which is incorporated herein by reference.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

DEFINITIONS

In describing and claiming the disclosed subject matter, the following terminology will be used in accordance with the definitions set forth below.

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, plastics (e.g., polyethylene oxide), nucleic acids and the like, where the polymers may be naturally occurring, non-naturally occurring, or synthetic.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). In addition, the protein can include non-standard and/or non-naturally occurring amino acids, as well as other amino acids that may be found in phosphorylated proteins in organisms such as, but not limited to, animals, plants, insects, protists, fungi, bacteria, algae, single-cell organisms, and the like. The non-standard amino acids include, but are not limited to, selenocysteine, pyrrolysine, gamma-aminobutyric acid, carnitine, ornithine, citrulline, homocysteine, hydroxyproline, hydroxylysine, sarcosine, and the like. The non-naturally occurring amino acids include, but are not limited to, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homo-glutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine.

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide includes conservatively modified variants. A substituted or inserted amino acid residue may or may not be one encoded by the genetic code. A variant of a polypeptide may be naturally occurring, such as an allelic variant, or it may be a variant that is not known to occur naturally.

Modifications and changes can be made in the structure of the polypeptides of this disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also means the degree of sequence relatedness between polypeptides as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an E. coli S30 extract and commercially available enzymes and other reagents. Proteins are purified by chromatography. (Robertson, et al., J. Am. Chem. Soc., 113: 2722, 1991; Ellman, et al., Methods Enzymol., 202: 301, 1991; Chung, et al., Science, 259: 806-9, 1993; and Chung, et al., Proc. Natl. Acad. Sci. USA, 90: 10145-9, 1993). In a second method, translation is carried out in Xenopus oocytes by microinjection of mutated mRNA and chemically aminoacylated suppressor tRNAs (Turcatti, et al., J. Biol. Chem., 271: 19991-8, 1996). Within a third method, E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide, et al., Biochem., 33: 7470-6, 1994). Naturally occurring amino acid residues can be converted to non-naturally occurring species by in vitro chemical modification. Chemical modification can be combined with site-directed mutagenesis to further expand the range of substitutions (Wynn, et al., Protein Sci., 2: 395-403, 1993).

As used herein, the term "polynucleotide" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. Polynucleotide encompasses the terms "nucleic acid," "nucleic acid sequence," or "oligonucleotide" as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alias.

By way of example, a polynucleotide sequence of the present disclosure may be identical to the reference sequence, that is be 100% identical, or it may include up to a certain integer number of nucleotide alterations as compared to the reference sequence. Such alterations are selected from the group including at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the reference nucleotide by the numerical percent of the respective percent identity (divided by 100) and subtracting that product from said total number of nucleotides in the reference nucleotide. Alterations of a polynucleotide sequence encoding the polypeptide may alter the polypeptide encoded by the polynucleotide following such alterations.

The term "codon" means a specific triplet of mononucleotides in the DNA chain. Codons correspond to specific amino acids (as defined by the transfer RNAs) or to start and stop of translation by the ribosome.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (e.g., GAU and GAC triplets each encode Asp).

By "administration" is meant introducing a compound into a subject. The preferred route of administration of the compounds is intravenous. However, any route of administration, such as oral, topical, subcutaneous, peritoneal, intraarterial, inhalation, vaginal, rectal, nasal, introduction into the cerebrospinal fluid, or instillation into body compartments can be used.

As used herein, the term "host" or "organism" includes humans, mammals (e.g., cats, dogs, horses, etc.), living cells, and other living organisms. A living organism can be as simple as, for example, a single eukaryotic cell or as complex as a mammal. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. In some embodiments, a system includes a sample and a host.

The term "sample" can refer to a tissue sample, cell sample, a fluid sample, and the like. The sample may be taken from a host. The tissue sample can include hair (including roots), buccal swabs, blood, saliva, semen, muscle, or from any internal organs. The fluid may be, but is not limited to, urine, blood, ascites, pleural fluid, spinal fluid, and the like. The body tissue can include, but is not limited to, skin, muscle, endometrial, uterine, and cervical tissue. In the present disclosure, the source of the sample is not critical.

The term "detectable" refers to the ability to detect a signal over the background signal.

The term "acoustic detectable signal" is a signal derived from a non-fluorescent absorber compound that absorbs light and converts absorbed energy into thermal energy that causes generation of acoustic signal through a process of thermal expansion. The acoustic detectable signal is detectable and distinguishable from other background acoustic signals that are generated from the host. In other words, there is a measurable and statistically significant difference (e.g., a statistically significant difference is enough of a difference to distinguish among the acoustic detectable signal and the background, such as about 0.1%, 1%, 3%, 5%, 10%, 15%, 20%, 25%, 30%, or 40% or more difference between the acoustic detectable signal and the background) between acoustic detectable signal and the background. Standards and/or calibration curves can be used to determine the relative intensity of the acoustic detectable signal and/or the background.

General Discussion

Embodiments of the present disclosure include photoacoustic probes, methods of making photoacoustic probes, methods of imaging, and the like. Embodiments of the photoacoustic probes are able to detect one or more targets (e.g., cells, tissue, chemicals, enzymes, and the like) by detecting the generation and/or reduction of a fluorescent signal and/or an acoustic signal. The term "detecting" refers to detecting a signal generated by one or more photoacoustic probes. It should be noted that reference to detecting a signal from a photoacoustic probe also includes detecting a signal from a plurality of photoacoustic probes. In some embodiments, a signal may only be detected that is produced by a plurality of photoacoustic probes. Additional details regarding detecting signals (e.g., acoustic signals) are described below. The photoacoustic probes can be used to provide high optical and/or acoustic contrast for imaging. In this regard, the photoacoustic probes can be used for imaging anatomical and/or physiological events in a host. Embodiments of the present disclosure enable the imaging of molecular events in vitro or in vivo using photoacoustic techniques and methods. The image acquired using the photoacoustic probes can be used to illustrate the concentration and/or location of the photoacoustic probes.

The term "acoustic signal" refers to a sound wave produced by one of several processes, methods, interactions, or the like (including light absorption) that provides a signal that can then be detected and quantitated with regards to its frequency and/or amplitude. The acoustic signal can be generated from one or more photoacoustic probes. In an embodiment, the acoustic signal may need to be sum of each of the individual photoacoustic probes or groups of photoacoustic probes. In an embodiment, the acoustic signal can be generated from a summation, an integration, or other mathematical process, formula, or algorithm, where the acoustic signal is from one or more photoacoustic probes. In an embodiment, the summation, the integration, or other mathematical process, formula, or algorithm can be used to generate the acoustic signal so that the acoustic signal can be distinguished from background noise and the like. It should be noted that signals other than the acoustic signal can be processed or obtained is a similar manner as that of the acoustic signal.

An advantage of an embodiment of the photoacoustic probe is that it provides a photoacoustic probe that is "silent" until interaction with the target, while another embodiment of the photoacoustic probe is always "active", each embodiment is discussed in more detail below.

It should be noted that a single type of photoacoustic probe could be used to image two distinct features (e.g., a target and an associated enzyme), as discussed in more detail herein. In addition, different types of photoacoustic probes can be used to image two or more distinct targets.

In an embodiment, the photoacoustic probe includes a targeting moiety and a non-fluorescent absorber compound that can generate an acoustic signal under appropriate conditions (described herein). The target moiety has an affinity for a target. The photoacoustic probe can accumulate at the target or target location. Upon excitation with a pulsed light (an optical signal) of appropriate wavelength (which depends upon the non-fluorescent absorber selected), the photoacoustic probe(s) can generate a detectable acoustic signal when the non-fluorescent absorber compound absorbs light and converts absorbed energy into thermal energy that causes generation of the acoustic signal through a process of thermal expansion. In other words, the non-fluorescent absorber compound has the characteristic of being able to absorb optical energy and being able to convert the absorbed energy to thermal energy to produce a detectable acoustic signal. Thus, the presence and/or location of the target can be detected and/or imaged by detecting the acoustic signal generated by the photoacoustic probe.

In another embodiment, the photoacoustic probe includes a target moiety, one or more fluorescent compounds that can generate a fluorescent signal under appropriate conditions (described herein), and a non-fluorescent absorber compound that can generate a detectable acoustic signal under appropriate conditions (described herein). In particular, the photoacoustic probe can generate a fluorescent signal when a fluorescent compound absorbs light. In addition, the photoacoustic probe can generate an acoustic signal when the non-fluorescent absorber compound absorbs the light and converts absorbed light into thermal energy that causes generation of acoustic signal. Typically, the photoacoustic probe only generates or significantly generates (e.g., the acoustic signal generated by the non-fluorescent absorber in the presence of the fluorescent absorber is less than about 5%, less than about 10%, or less than about 15%) one of the fluorescent signal or the acoustic signal. For example, initially the photoacoustic probe generates a fluorescent signal upon absorption of the optical energy. Subsequently, under certain conditions (e.g., presence of one or more targets (e.g., enzyme)), the fluorescent signal is decreased or eliminated (e.g., the fluorescent compound is released from or made separate from the photoacoustic probe or the target interacts with the fluorescent compound so it can not absorb the optical energy) and the acoustic signal is generated. Additional details regarding embodiments of the present disclosure are described in more detail herein and in the examples.

As mentioned above, an embodiment of the photoacoustic probe includes, but is not limited to, a targeting moiety and a non-fluorescent absorber compound. The targeting moiety is linked (directly or indirectly) to the non-fluorescent absorber compound. FIG. 1 illustrates an embodiment of the photoacoustic probe 10a having the targeting moiety 12 and the non-fluorescent absorber compound 14.

Figure 2:
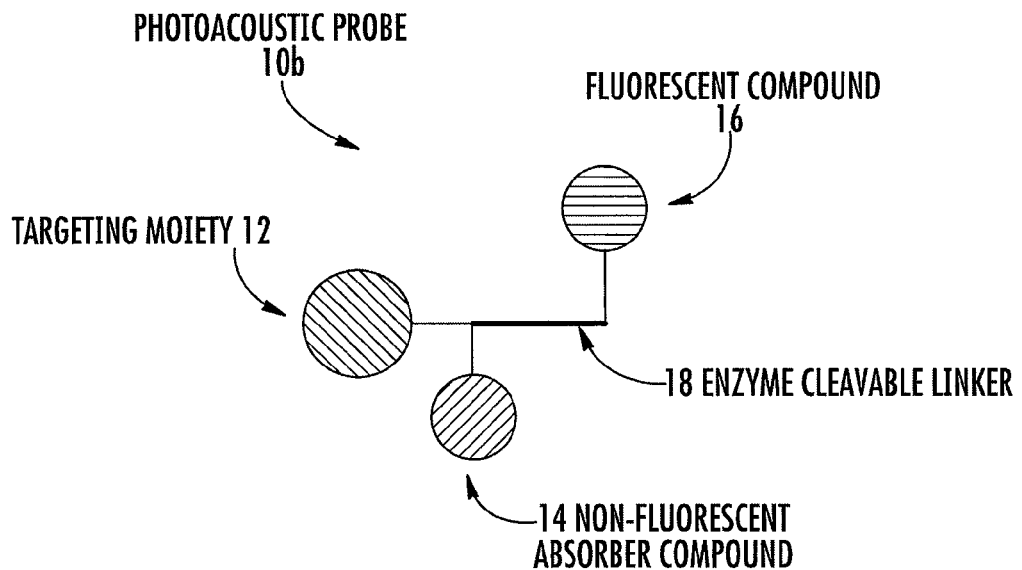
FIG. 2 illustrates an embodiment of the photoacoustic probe.

Another embodiment of the photoacoustic probe includes, but is not limited to, a targeting moiety, a non-fluorescent absorber compound, an enzyme cleavable linker, and a fluorescent compound. In an embodiment, two or more fluorescent compounds can be used. The targeting moiety is linked (directly or indirectly) to the non-fluorescent absorber compound and the enzyme cleavable linker, while the enzyme cleavable linker is linked to the fluorescent compound. Embodiments of the photoacoustic probe can include the components of the photoacoustic probe linked in one or more configurations using one or more types of linkers. For example, FIG. 2 illustrates an embodiment of a photoacoustic probe 10b. The photoacoustic probe 10b includes a targeting moiety 12 linked to a non-fluorescent absorber compound 14 and an enzyme cleavable linker 18, while the enzyme cleavable linker 18 is linked to a fluorescent compound 16. FIG. 2 is a non-limiting embodiment, and other embodiments are contemplated and described herein. The components of the photoacoustic probes described above and in FIGS. 1 and 2 are described below.

In general, the targeting moiety can include, but is not limited to, polypeptides (e.g., proteins such as, but not limited to, antibodies (monoclonal or polyclonal)), nucleic acids (both monomeric and oligomeric), polysaccharides, sugars, fatty acids, steroids, purines, pyrimidines, ligands, or combinations thereof. The targeting moiety has an affinity for one or more targets. In general, the target can include, but is not limited to, a cell type, a cell surface, extracellular space, intracellular space, a tissue type, a tissue surface, the vascular, a polypeptide, a nucleic acid, a polysaccharide, a sugar, a fatty acid, a steroid, a purine, a pyrimidine, a hapten, a ligand, and the like, related to a condition, disease, or related biological event or other chemical, biochemical, and/or biological event of the sample or host. The targeting moiety can be selected based on the target selected and the environment the target is in and/or conditions that the target is subject to.

In particular, the targeting moiety can be specific or non-specific. The specific targeting moiety can be selected to have an affinity (e.g., an attraction to) for a target such as, but not limited to, a specific protein, a cell type, a receptor, a transporter, an antigen, and a saccharide (e.g., a monosaccharide, a disaccharide and a polysaccharide), as well as other molecules that can interact with the targeting moiety. The specific targeting moiety can include, but is not limited to, an antibody, an antigen, a polypeptide, an aptamer, a small molecule, and ligands, as well as other molecules that bind to the target. In an embodiment, molecules that can be targeted include, but are not limited to, vascular receptors (e.g., Vascular endothelial growth factor receptor (VEGF-R)), extracellular matrix proteins (e.g., proteases), cell membrane receptors (e.g., epidermal growth factor receptor (EGFR)), intracellular proteins, enzymes, and messenger RNA (mRNA).

The non-specific targeting moiety can be selected to do one or more of the following: enter a cell or a cell type, enter the vasculature, enter extracellular space, enter intracellular space, have an affinity for a cell surface, diffuse through a cell membrane, react with a non-specified moiety on the cell membrane, enter tumors due to leaky vasculature, and the like. In an embodiment, the non-specific targeting moiety can include a chemical, biochemical, or biological entity that facilitates the uptake of the photoacoustic probe into a cell. The non-specific targeting moiety can include, but is not limited to, cell penetrating peptides, polyaminoacid chains, small molecules, and peptide mimics.

In another embodiment, the photoacoustic probe is introduced to (e.g., injected or otherwise administered to) a sample or host, where the photoacoustic probe includes a specific targeting moiety and the non-fluorescent absorber compound. The specific targeting moiety has an affinity for a target, which causes the photoacoustic probe to become disposed adjacent to, attached to, disposed within the target, or otherwise interact with the target. The targeting moiety (e.g., RGD peptide (Arg-Gly-Asp) (corresponding to integrin $\alpha_v\beta_3$)) interacts with its specific target (e.g., integrin $\alpha_v\beta_3$), which causes the photoacoustic probe to become disposed adjacent to, attached to, disposed within the specific target, or otherwise interact with the target. Subsequently, the sample or host is subject to an optical energy. The optical energy (e.g., about 500 to 900 nm (wavelength range)) is absorbed by the non-fluorescent absorber compound and is converted into thermal energy to produce a detectable acoustic signal. In other words, the non-fluorescent absorber compound has the characteristic of being able to absorb optical energy and being able to convert the absorbed energy to thermal energy to produce a detectable acoustic signal. The production of the acoustic signal can be used to detect the presence of and the location of the specific target (e.g., integrin) in the sample or host. An image of the sample or host or portions thereof can be produced by detecting the acoustic signal, which is used to determine the presence and location of the target.

In another embodiment, the photoacoustic probe is introduced to (e.g., injected or otherwise administered to) a system (a sample or a host), where the photoacoustic probe includes a non-specific targeting moiety, the non-fluorescent absorber compound, the enzyme cleavable linker, and a fluorescent compound. The non-specific targeting moiety is linked to the non-fluorescent absorber compound and the enzyme cleavable linker, while the enzyme cleavable linker is linked to the fluorescent compound. The targeting moiety is a non-specific targeting moiety that has an affinity for a target (e.g., to enter a cell, vascular, or the like), which causes the photoacoustic probe to become disposed adjacent to, attached to, disposed within the target, or otherwise interact with the target. The non-specific targeting moiety interacts (as described above) with its non-specific target, which causes the photoacoustic probe to become disposed adjacent to, attached to, disposed within the non-specific target, or otherwise interact with the non-specific target. If the non-specific target includes or has an enzyme associated therewith (or another chemical of interest associated therewith), the enzyme interacts with the enzyme cleavable linker causing the fluorescent compound to be released from the photoacoustic probe. Subsequently, the optical energy is absorbed by the non-fluorescent absorber compound and is converted to thermal energy to produce the acoustic signal. The production of the acoustic signal indicates that the enzyme is present in the sample or host. An image of the sample or host or portions thereof can be produced by detecting the acoustic signal.

In another embodiment, the photoacoustic probe is introduced to (e.g., injected or otherwise administered to) a system (a sample or a host), where the photoacoustic probe includes a specific targeting moiety, the non-fluorescent absorber compound, the enzyme cleavable linker, and a fluorescent compound. The targeting moiety is a specific targeting moiety that has an affinity for a target, which causes the photoacoustic probe to become disposed adjacent to, attached to, disposed within the target, or otherwise interact with the target. The targeting moiety interacts with its specific target (e.g., integrin $\alpha_v\beta_3$), which causes the photoacoustic probe to become disposed adjacent to, attached to, disposed within the specific target, or otherwise interact with the target. If the target includes or has an enzyme (e.g., mmp-2) associated therewith (or another chemical of interest associated therewith), the enzyme interacts with the enzyme cleavable linker causing the fluorescent compound to be released from the photoacoustic probe. Subsequently, the optical energy is absorbed by the non-fluorescent absorber compound and is converted to thermal energy to produce a detectable acoustic signal. The production of the acoustic signal indicates that both the specific target (e.g., integrin) and enzyme (e.g., mmp-2) are present in the sample or host. An image of the sample or host or portions thereof can be produced by detecting the acoustic signal. Thus, the photoacoustic probe can produce images for two specific targets at the same time. It should also be noted that if the fluorescent signal is detected, then the target is present and the enzyme is not present. If no signal is detected, then the target is not present.

It should be noted that for the embodiments above, the fluorescent compound absorbs the optical energy and produces a fluorescent signal that can be detected prior to interaction with the enzyme or in the absence of the enzyme while the photoacoustic probe interacts with the target. The non-fluorescent absorber compound does not absorb or does not substantially absorb the optical energy prior to the release of the fluorescent compound. In this regard, the non-fluorescent absorber compound is in competition with the fluorescent compound to absorb the optical energy. Thus, the fluorescent compound absorbs most if not all of the optical energy since the fluorescent compound more efficiently absorbs the optical energy relative to the non-fluorescent absorber compound. As a result, the sample or host illuminated with the optical energy generates a fluorescent signal, but does not absorb an acoustic signal.

The non-fluorescent absorber compound should have one or more of the following characteristics: have high absorbance in the near infrared region, be non-fluorescent or substantially non-fluorescent, be a poor (e.g., does not absorb or does not substantially absorb energy from the fluorescent compound) quencher of the fluorescent compound (described below), have a lower extinction coefficient relative to the fluorescent compound (e.g., for the same concentration of the non-fluorescent absorber compound and fluorescent compound, the fluorescent compound absorbs more optical energy), produce detectable acoustic energy upon absorbing optical energy, be stable, be non-immunogenic, be non-toxic, have favorable pharmacokinetics (in terms of solubility in aqueous solutions), and/or be able to be conjugated to one or more of the other components or linkers, directly or indirectly.

The non-fluorescent absorber compound can include, but is not limited to small molecules such as diarylrhodamine derivatives (e.g., QSY-7, QSY-9, and QSY-21); polyaromatic-azo quenchers (e.g., BHQ 2 and BHQ 3); Blackberry Q; and bisazulene derivatives, as well as non-fluorescent absorbing nanoparticles (e.g., carbon nanotubes, gold nanoparticles, and the like). In an embodiment, the non-fluorescent absorber compound can be replaced with a fluorescent compound that has a poor quantum yield (e.g., most of the energy is not irradiated but lost through heat).

The acoustic energy can be detected and quantified in real time using an appropriate detection system. The acoustic signal can be produced by one or more photoacoustic probes. One possible system is described in the following references: Journal of Biomedical Optics—March/April 2006—Volume 11, Issue 2, 024015, Optics Letters, Vol. 30, Issue 5, pp. 507-509, each of which are included herein by reference. In an embodiment, the acoustic energy detection system can includes a 5 MHz focused transducer (25.5 mm focal length, 4 MHz bandwidth, F number of 2.0, depth of focus of 6.5 mm, lateral resolution of 600 μm, and axial resolution of 380 μm. A309S-SU-F-24.5-MM-PTF, Panametrics), which can be used to acquire both pulse-echo and photoacoustic images. In addition, high resolution ultrasound images can also be simultaneously acquired using a 25 MHz focused transducer (27 mm focal length, 12 MHz bandwidth, F number of 4.2, depth of focus of 7.5 mm, lateral resolution of 250 μm, and axial resolution of 124 μm. V324-SU-25.5-MM, Panametrics). Other detection strategies including capacitive micromachined ultrasonic transducers (CMUT) arrays can also be used to detect the acoustic signal.

The fluorescent compound should have one or more of the following characteristics: be able to convert all of or substantially all of the absorbed optical energy into fluorescence energy and poorly convert or not convert the absorbed optical energy into thermal energy, be poorly quenched or not quenched by the non-fluorescent absorber compound, have a extinction coefficient much higher relative to the non-fluorescent absorber compound, be non toxic, be non-immunogenic, and/or have favorable pharmacokinetics. In an embodiment, two or more fluorescent compound could be used and each can include one or more of the characteristics noted above.

The fluorescent compound can include NIR dyes. The NIR dyes can include, but are not limited to, BODIPY® fluorophores (Molecular Probes) (e.g., 4,4-difluoro-4-bora-3a,4a-diaza-s-indacene (and derivatives thereof), which can be modified to alter the wavelength (BODIPY® substitutes for the fluorescein, rhodamine 6G, tetramethylrhodamine and Texas Red fluorophores are BODIPY® FL, BODIPY® R6G, BODIPY® TMR and BODIPY® TR, respectively)), 1H,5H, 11H,15H-Xantheno[2,3,4-ij:5,6,7-i'j']diquinolizin-18-ium, 9-[2(or 4)-(chlorosulfonyl)-4(or 2)-sulfophenyl]-2,3,6,7,12,13,16,17-octahydro-, inner salt (molecular formula: $C_{31}H_{29}ClN_2O_6S_2$) (and derivatives thereof) (Texas Red), Xanthylium, 3,6-diamino-9-(2-(methoxycarbonyl)phenyl, chloride ($C_{21}H_{17}ClN_2O_3$) (and derivatives thereof) (NIR Rhodamine dye), and cyanine dyes (and derivatives thereof), where derivatives of each can be used to modify the wavelength. In particular, the fluorescent compound can include, but is not limited to, BODIPY® dye series (e.g., BODIPY® FL-X, BODIPY® R6G-X, BODIPY® TMR-X, BODIPY® TR-X, BODIPY® 630/650-X, and BODIPY® 650/665-X (Molecular Probes, Inc. Eugene, Oreg., USA)), NIR Rhodamine dyes, NIR Alexa® dyes (e.g., Alexa® Fluor 350, Alexa® Fluor 405, Alexa® Fluor 430, Alexa® Fluor 488, Alexa® Fluor 500 (Molecular Probes, Inc. Eugene, Oreg., USA)), Texas Red, or cyanine dyes (e.g., Cy5.5 Cy3, Cy5), and Li-Cor IRDye™ products. Additional guidance regarding the fluorescent compound and the non-fluorescent absorber compound is provided in FIG. 10 (www.umass.edu/research/genomics).

The fluorescent energy can be detected and quantified in real time using an appropriate detection system (e.g., a photomultiplier tube in a fluorometer and/or a luminometer, for example).

The enzyme cleavable linker is a compound or a polymer (e.g., polypeptide sequence) that can be cleaved or broken by the interaction (e.g., chemically, biologically, biochemically, and/or physically) of the enzyme cleavable linker with a target enzyme. The target enzyme linker interacts with (e.g., a chemical, a biological, or biochemical reaction) and cleaves, breaks, or otherwise causes the enzyme cleavable linker to release the fluorescent compound to be a separate entity. The enzyme cleavable linker can include, but is not limited to, a chemical compound, a polypeptide, a protein, saccharides, lipids, polynucleotides, and combinations thereof. In particular, the enzyme cleavable linker can include, but is not limited to, DEVD, PLGVRG, PQGIMG, polylysine chain, G-R-F-G, and combinations thereof. In addition, the enzyme cleavable linker can include compounds or polymers that can be cleaved by enzymes such as, but not limited to glycosidases, lyases, hydrolases, nucleases, mmp-2, mmp-9, cathepsin B, caspase-3, other proteases. Proteases are a general group of enzymes capable of cleaving amide bonds.

The targeting moiety, the non-fluorescent absorber compound, the enzyme cleavable linker, and the fluorescent compound each can be linked, directly or indirectly, in a manner described above using a stable physical, biological, biochemical, and/or chemical association. In general, the targeting moiety, the non-fluorescent absorber compound, the enzyme cleavable linker, and the fluorescent compound each can be independently linked via chemical bonding (e.g., covalently or ionically), biological interaction, biochemical interaction, and/or otherwise associated with one another in a manner described above. The targeting moiety, the non-fluorescent absorber compound, the enzyme cleavable linker, and the fluorescent compound each can be independently linked using, but not limited to, a covalent link, a non-covalent link, an ionic link, a chelated link, as well as being linked through interactions such as, but not limited to, hydrophobic interactions, hydrophilic interactions, charge-charge interactions, π-stacking interactions, combinations thereof, and like interactions.

The linker can be a compound or polymer (e.g., a polypeptide and/or a polynucleotide) that includes one or more functional groups to attach one or more the targeting moiety, the non-fluorescent absorber compound, the enzyme cleavable linker, and the fluorescent compound. The linker can include functional groups such as, but not limited to, amines, carboxylic acids, hydroxyls, thiols, and combinations thereof. The linker can include compounds such as, but not limited to, diethylene triamine pentaacetic acid (DTPA), ethylenediaminetetraacetic acid (EDTA), 3,4-dihydroxyphenylalanine (DOPA), ethylene glycol tetraacetic acid (EGTA), nitrilotriacetic acid (NTA), and combinations thereof.

It should be noted that an agent could be included in the photoacoustic probe. The agent can be linked to one of the targeting moiety or the non-fluorescent absorber compound (directly or indirectly). The agent can include, but is not limited to, polypeptides (e.g., protein such as, but not limited to, an antibody (monoclonal or polyclonal)), nucleic acids (both monomeric and oligomeric), polysaccharides, sugars, fatty acids, steroids, purines, pyrimidines, drugs (e.g., small compound drugs), ligands, photosensitizers, or combinations thereof.

In addition, the agent can also include, but is not limited to, a drug, a therapeutic agent, radiological agent, photosensitizers, a small molecule drug, and combinations thereof, that can be used to treat the target molecule and/or the associated disease and condition of interest. The drug, therapeutic agent, and radiological agent can be selected based on the intended treatment as well as the condition and/or disease to be treated. In an embodiment, the photoacoustic probe can include two or more agents used to treat a condition and/or disease. In addition, the detection of the photoacoustic probe can be used to ensure the delivery of the agent or drug to its intended destination as well as the quantity of agent or drug delivered to the destination.

In particular, the photoacoustic probes can be used in in-vivo diagnostic and/or therapeutic applications such as, but not limited to, targeting diseases and/or conditions and/or imaging diseases and/or conditions. For example, one or more embodiments of the photoacoustic probes can be used to identify the type of disease or condition, identify the presence of one or more compounds associated with the disease or condition, locate the proximal locations of the disease or condition, and/or deliver agents (e.g., drugs) to the diseased cells (e.g., cancer cells, tumors, and the like) in living animals.

Methods of Use

As mentioned above, the present disclosure relates generally to methods for studying (e.g., detecting, localizing, and/or quantifying) cellular events, molecular events, in vivo cell trafficking, stem cell studies, vascular imaging, tumor imaging, biomolecule array systems, biosensing, biolabeling, gene expression studies, protein studies, medical diagnostics, diagnostic libraries, microfluidic systems, and delivery vehicles. The present disclosure also relates to methods for multiplex imaging of multiple events substantially simultaneously inside a subject (e.g., a host living cell, tissue, or organ, or a host living organism) using one or more photoacoustic probes.

In short, the photoacoustic probes are introduced to the system (sample or host) using known techniques (e.g., injection, oral administration, and the like) to determine if the system includes one or more targets (e.g., a target with or without a chemical (enzyme) associated with the target). At an appropriate time, the sample (e.g., living cell, tissue, or organ) or host is illuminated with an optical energy. In an embodiment, the appropriate time may include a time frame to allow unassociated photoacoustic probes to be sufficiently cleared from the appropriate area, region, or tissue of interest.

The fluorescence signal or reduction of the fluorescence signal and/or the detection of the acoustic signal can be measured using systems described herein. In an embodiment, the production of the acoustic signal in conjunction with the reduction or loss of the fluorescent signal indicates that the photoacoustic probe(s) has interacted with the target and that the enzyme is in close proximity of the target. In other words, the photoacoustic probe(s) is able to detect the presence of both the target and the enzyme. In another embodiment, the production of the acoustic signal indicates that the target is present in the sample or host.

The fluorescent signal and/or the acoustic signal can be detected and quantified in real time using a detection system. The measured signal is or can be correlated to the feature being studied. In an embodiment, the detection of the fluorescent signal and/or the acoustic signal can be conducted after a sufficient time frame to allow unassociated photoacoustic probes to be sufficiently cleared from the appropriate area, region, or tissue of interest.

In an embodiment, the photoacoustic probes can be used to study, image, diagnose the presence of, and/or treat cancerous cells, precancerous cells, cancer, or tumors and/or chemical (enzymes) associated with the cancerous cells, precancerous cells, cancer, or tumors. For example, the presence of the cancerous cells, precancerous cells, cancer, or tumors in conjunction with a chemical (e.g., enzyme) can provide insight into the appropriate diagnosis and/or treatment. It should be noted that photoacoustic probes could include agents specific for other diseases or conditions so that other diseases or conditions can be imaged, diagnosed, and/or treated using embodiments of the present disclosure. In an embodiment, other diseases and/or conditions can be studied, imaged, diagnosed, and/or treated in a manner consistent with the discussion below as it relates to cancerous cells, precancerous cells, cancer, and/or tumors.

In another embodiment, the photoacoustic probes include one or more agents to treat the cancerous cells, precancerous cells, cancer, or tumors. Upon measuring the fluorescent signal and/or the acoustic signal, one can determine if the photoacoustic probe has coordinated with the cancerous cells, precancerous cells, cancer, or tumors. Embodiments of the photoacoustic probe can aid in visualizing the response of the cancerous cells, precancerous cells, cancer, or tumors to the agent.

In general, the photoacoustic probes can be used in a screening tool to select agents for imaging, diagnosing, and/or treating a disease or condition. In an embodiment, the photoacoustic probes can be used in a screening tool to select agents for imaging, diagnosing, and/or treating cancerous cells, precancerous cells, cancer, or tumors. The photoacoustic probes can be imaged and it can be determined if each agent can be used to image, diagnose, and/or treat cancerous cells, precancerous cells, cancer, or tumors.

Kits

This disclosure encompasses kits that include, but are not limited to, photoacoustic probes (e.g., with one or more agents as described above) and directions (written instructions for their use). The components listed above can be tailored to the particular cellular event being studied, imaged, and/or treated (e.g., cancer, cancerous, or precancerous cells). The kit can further include appropriate buffers and reagents known in the art for administering various combinations of the components listed above to the host cell or host organism.

EXAMPLES

Now having described the embodiments of photoacoustic probes, systems, and methods of use, in general, the examples describe some additional embodiments of the present disclosure. While embodiments of present disclosure are described in connection with the examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Discussion

Figure 3:
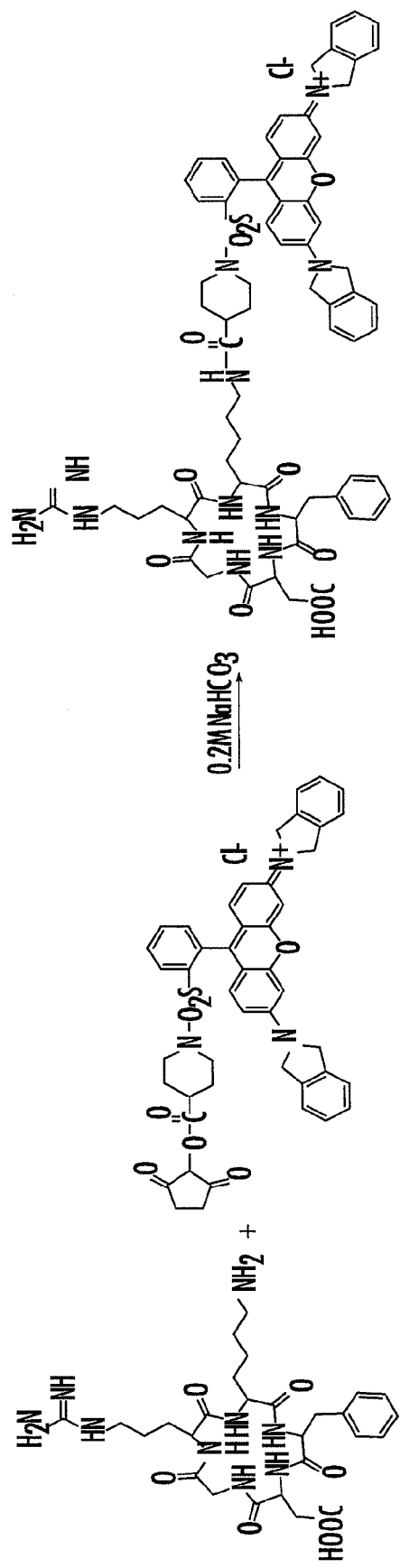
FIG. 3 illustrates the synthesis of RGD-QSY-21.
Figure 4:
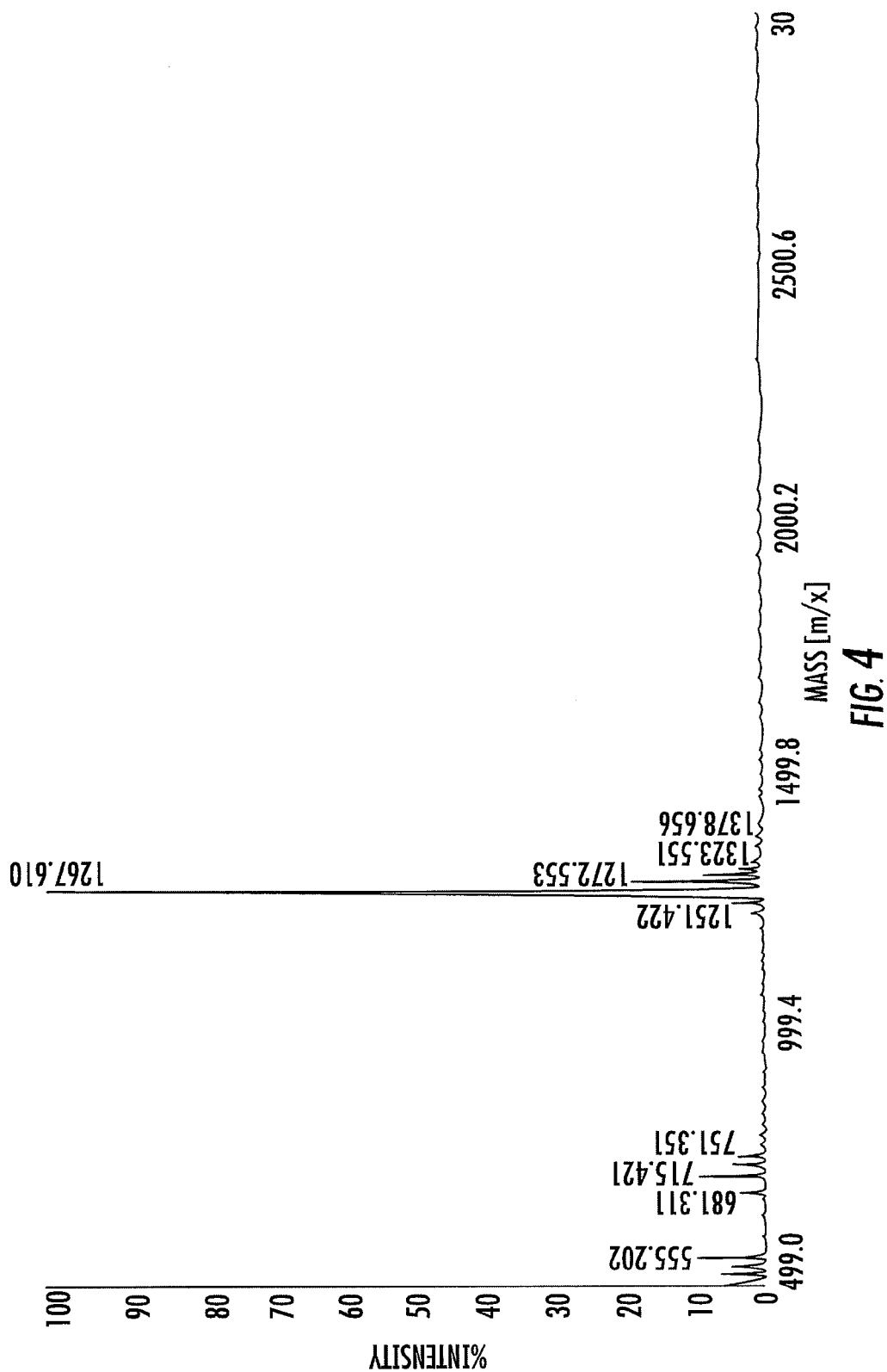
FIG. 4 illustrates a MALDI-TOF spectrum that was used to determine molecular weight (1267.6 g/mol) of RGD-QSY-21.
Figure 5:
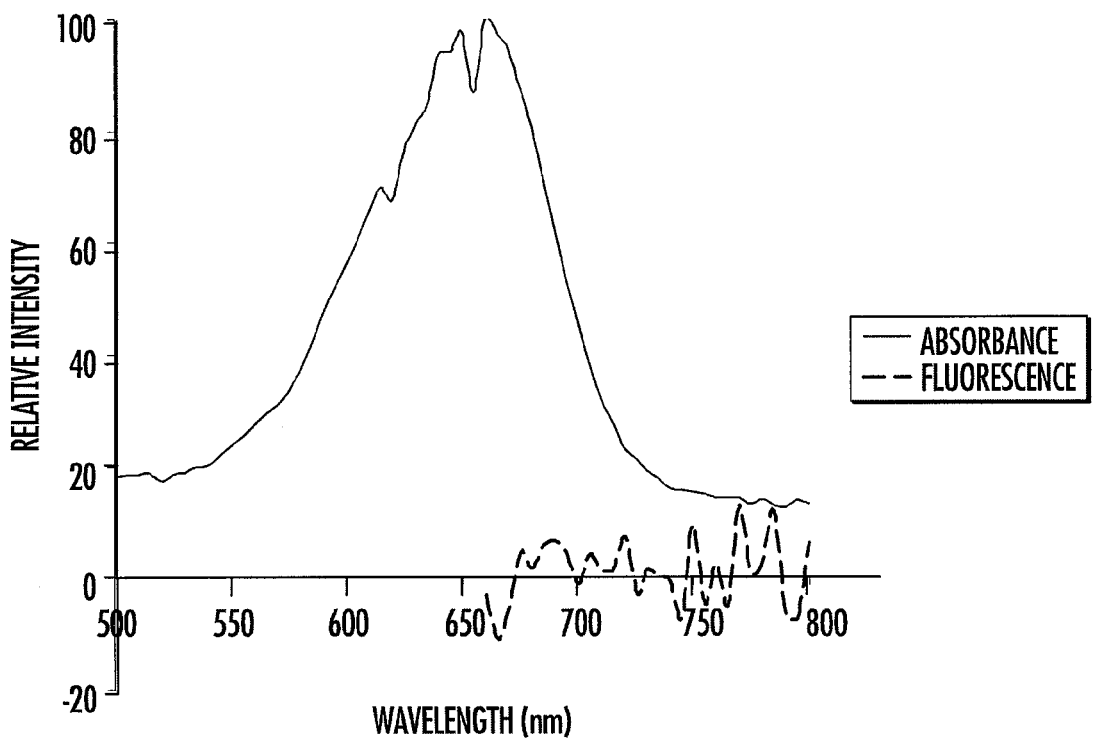
FIG. 5 illustrates a spectrum of the RGD-QSY-21 conjugate, which had a maximum absorbance wavelength of 660 nm, while not fluorescing.

Synthesis of the RGD-QSY-21 (RGD refers to three amino acids (Arg-Gly-Asp) and QSY is a optical dye):

FIG. 3 illustrates the synthesis of RGD-QSY-21. About 0.8 mg of RGD peptide was dissolved in about 40 μL 0.2 M NaHCO$_3$ (pH 8.3). About 1.12 mg of QSY-21 NHS ester dissolved in 100 μL DMSO was added to the solution. The mixture was kept at room temperature for about 1 hour, and then at 4° C. overnight. The product mixture was diluted with water and injected onto HPLC column. Retention time of the product was determined to be 30.1 min. MALDI-TOF was used to determine molecular weight (1267.6 g/mol) (FIG. 4). RGD-QSY-21 conjugate was spectrally characterized and had a maximum absorbance wavelength of 660 nm, while not fluorescing (FIG. 5).

Figure 6:
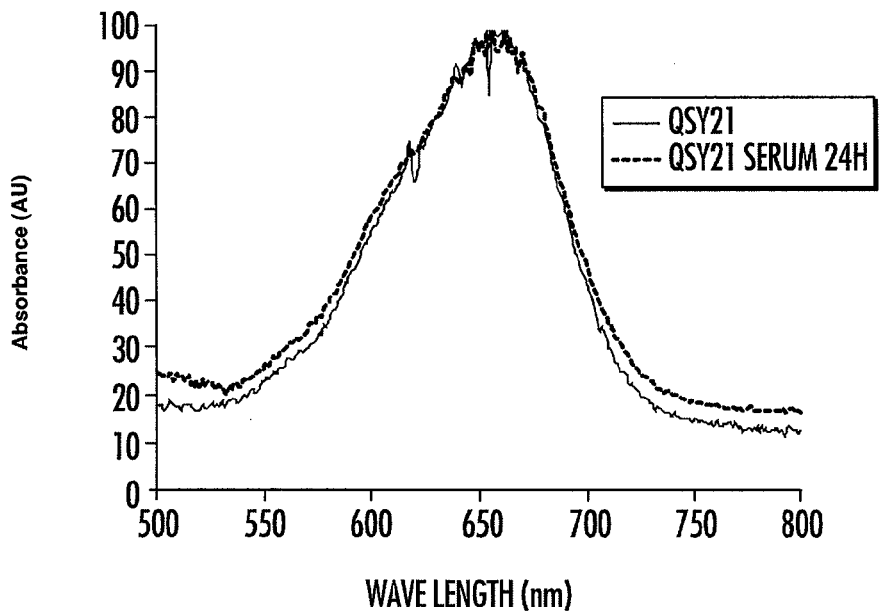
FIG. 6 illustrates a graph comparing QSY-21 and QSY-21 (serum 24h).

Serum stability of the RGD-QSY21 conjugate was determined by incubating methanolic solution of RGD-QSY 21 (50 μl) with 1 mL mouse serum. At 2 hours and at 24 hours absorbance of the mixture was measured and determined to be the same as the original absorbance-indicating stability of the probe in the serum (FIG. 6).

Figure 7:
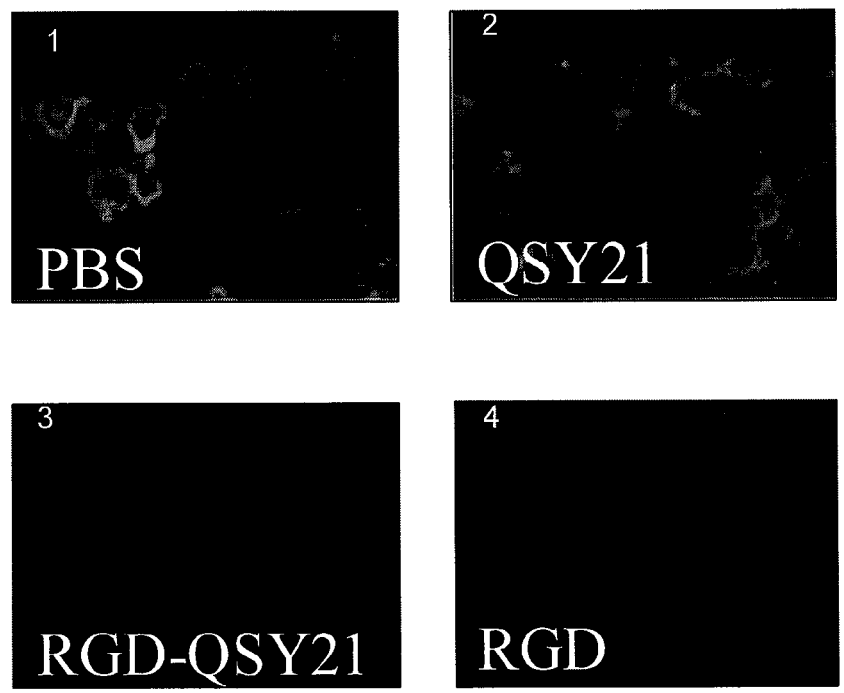
FIGS. 7(1)-7(4) illustrate digital images of cells that were incubated for 1 hour with PBS (FIG. 7(1)), QSY-21 (FIG. 7(2)), RGF-QSY21 (FIG. 7(3)), and RGF (FIG. 7(4)). Then the cells were incubated for ½ hour with Alexa488 conjugated $\alpha_v\beta_3$ integrin antibody. The results indicate retention of the targeting ability of the integrin targeting moiety (RGD) of the conjugate. In addition, the cells incubated with PBS and unconjugated QSY-21 (negative controls) show no inhibition of the antibody binding, while cells incubated with RGD-QSY21 and RGD show inhibition of antibody binding.
Figure 8:
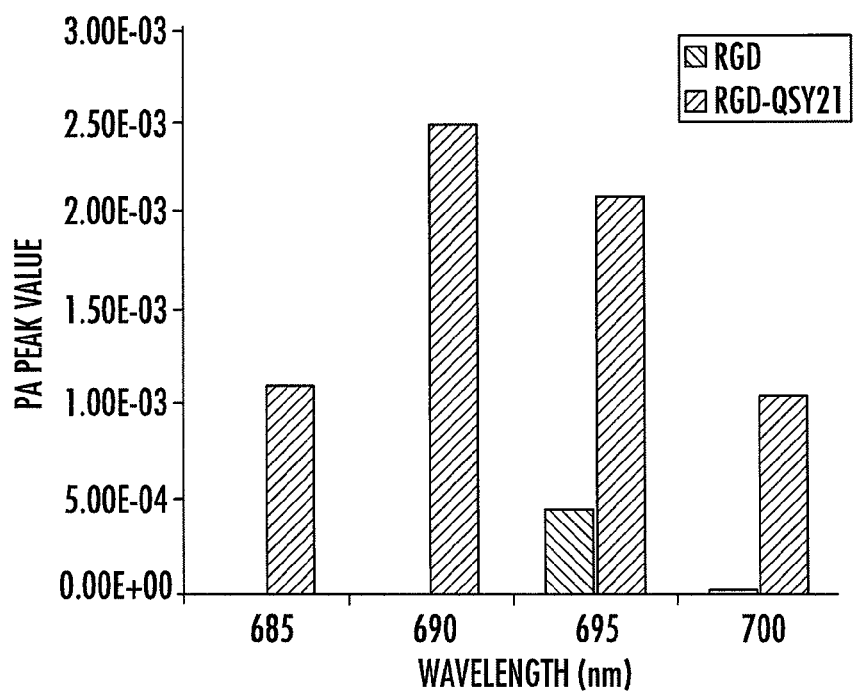
FIG. 8 illustrates a graph of a comparison of RGD and RGD-QSY21 conjugate that shows that conjugation does not change the activity of the RGD part of the conjugate.

Targeting ability of the conjugate was tested by imaging inhibition of the avb3 intergrin antibody. Cells were incubated for 1 hour with PBS (FIG. 7(1)), QSY-21 (FIG. 7(2)), RGD-QSY21 (FIG. 7(3)), and RGD (FIG. 7(4)). Then the cells were incubated for ½ hour with Alexa488 conjugated $\alpha_v\beta_3$ integrin antibody. The results indicate retention of the targeting ability of the integrin targeting moiety (RGD) of the conjugate. In addition, the cells incubated with PBS and unconjugated QSY-21 (negative controls) show no inhibition of the antibody binding, while cells incubated with RGD-QSY21 and RGD show inhibition of antibody binding. Comparison of RGD and RGD-QSY21 conjugate (FIG. 8) shows that conjugation does not change the activity of the RGD part of the conjugate.

Figure 9:
FIG. 9 illustrates the synthesis of an embodiment of a probe of the present disclosure.
Figure 9:

Synthesis of an Additional Probe (FIG. 9):

About 750 μg peptide (Arg-Arg-Arg-Arg-Arg-Lys-Pro-Leu-Gly-Val-Arg-Cys-NH$_2$) (SEQ ID NO: 1) was dissolved in 100 μL degassed PBS. About 890 μg of QSY-21 NHS in 75 μL DMF and about 950 μg of CY5.5-maleimide in 75 μl DMF was added to the solution. The mixture was held at room temperature for 1 hour and then overnight at 4° C. The mixture was analyzed using HPLC. The product was collected (retention time 26.1 min) and molecular weight detected by MALDI (3299 g/mol).

Example 2

U 87MG cells will be exposed to the photoacoustic probes and their photoacoustic signal detected.

Photoacoustic probes will be injected in mice carrying tumors expressing intergrin α3βv, such as glioma U87 MG, and imaged using photoacoustic systems as described above. Specificity of the probes for intergrin expressing tumors will be determined.

Specificity of the smart photoacoustic probes will be determined by exposing probes to cells having and not having mmp-2. Smart photoacoustic probes will be injected in mice carrying tumors that express mmp-2 and mice imaged using photoacoustic system. Specificity of the photoacoustic probes for tumors expressing mmp-2 will be determined.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

being able to generate a fluorescent signal, wherein the non-fluorescent absorber compound has the characteristic of being able to absorb the optical energy and being able to convert the absorbed energy to thermal energy to produce an acoustic signal, wherein the fluorescent compound more efficiently absorbs the optical energy relative to the non-fluorescent absorber compound, wherein the enzyme cleavable linker is capable of being cleaved by an enzyme so that the fluorescent compound is not attached to the photoacoustic probe, wherein the photoacoustic probe is configured to only significantly generate the fluorescent signal when the fluorescent compound is attached to the photoacoustic probe, and wherein the photoacoustic probe is configured to generate the acoustic signal when the fluorescent compound is not attached to the photoacoustic probe, and wherein the fluorescent absorber compound is a near infrared (NIR) dye.

2. The photoacoustic probe of claim 1, wherein the targeting moiety is a specific targeting moiety.

3. The photoacoustic probe of claim 1, wherein the non-fluorescent absorber compound is selected from the group consisting of: diarylrhodamine derivatives, polyaromatic-azo quenchers, Blackberry Q, bisazulene derivatives, non-fluorescent absorbing nanoparticles, and a combination thereof.

4. The photoacoustic probe of claim 1, wherein the fluorescent absorber compound is selected from the group consisting of: 4-difluoro-4-bora-3a,4a-diaza-s-indacene; 1H,5H,11H,15H-Xantheno[2,3,4-ij:5,6,7-i'j']diquinolizin-18-ium, 9-[2(or 4)-(chlorosulfonyl)-4(or 2)-sulfophenyl]-2,3,6,7,12,13,16,17-octahydro-, inner salt; Xanthylium, 3,6-diamino-9-(2-(methoxycarbonyl)phenyl, chloride; cyanine dye, and derivatives of each.

5. The photoacoustic probe of claim 1, wherein the enzyme cleavable linker is selected from: diethylene triamine pen-

---

---

We claim the following:

1. A photoacoustic probe comprising: a targeting moiety, a non-fluorescent absorber compound, an enzyme cleavable linker, and a fluorescent compound, wherein the targeting moiety is linked to the non-fluorescent absorber compound and the enzyme cleavable linker, while the enzyme cleavable linker is linked to the fluorescent compound such that the fluorescent compound is separated from the targeting moiety and the non-fluorescent absorber compound by the enzyme cleavable linker, wherein the fluorescent compound has the characteristic of being able to absorb an optical energy and taacetic acid (DTPA), ethylenediaminetetraacetic acid (EDTA), 3,4-dihydroxyphenylalanine (DOPA), ethylene glycol tetraacetic acid (EGTA), nitrilotriacetic acid (NTA), and combinations thereof.

6. The photoacoustic probe of claim 1, wherein the targeting moiety is selected from: an antibody, an antigen, a polypeptide, an aptamer, a small molecule, or a ligand, that binds to a target.

* * * * *

UNITED STATES PATENT AND TRADEMARK OFFICE
CERTIFICATE OF CORRECTION

PATENT NO.        : 8,574,547 B2                                               Page 1 of 1
APPLICATION NO.   : 12/595525
DATED             : November 5, 2013
INVENTOR(S)       : Gambhir et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 662 days.

Signed and Sealed this
Twenty-second Day of September, 2015

Michelle K. Lee
*Director of the United States Patent and Trademark Office*

SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Chemically synthesized peptide sequence for
      photoacoustic probe

<400> SEQUENCE: 1

Arg Arg Arg Arg Arg Lys Pro Leu Gly Val Arg Cys
1               5                   10